United States Patent [19]
Johnson et al.

[11] Patent Number: 5,910,419
[45] Date of Patent: Jun. 8, 1999

[54] METHOD FOR FORENSICALLY SCREENING HAIR SAMPLES FOR THE PRESENCE OF CANNABINOIDS

[76] Inventors: Ted Donald Johnson, 5239 Martingale Ave., Las Vegas, Nev. 89119; W. Craig Brown, 3417 Baldoyle La., Las Vegas, Nev. 89129; Raymond C. Kelly, 3302 E. Oquendo Rd., Las Vegas, Nev. 89120

[*] Notice: This patent is subject to a terminal disclaimer.

[21] Appl. No.: 08/851,735

[22] Filed: May 6, 1997

[51] Int. Cl.⁶ .............................. G01N 33/53; G01N 1/00
[52] U.S. Cl. ........................... 435/7.92; 435/7.9; 435/7.1; 436/174
[58] Field of Search ..................... 435/7.92, 7.1, 435/975, 7.91; 436/901, 815, 174, 175, 176

[56] References Cited

U.S. PATENT DOCUMENTS

| | | |
|---|---|---|
| 3,623,950 | 11/1971 | Monsheimer et al. . |
| 3,966,551 | 6/1976 | Monsheimer et al. . |
| 3,986,926 | 10/1976 | Monsheimer et al. . |
| 4,438,207 | 3/1984 | Fahrenholtz et al. ............... 436/543 |
| 4,454,232 | 6/1984 | Brelio et al. ........................ 436/504 |
| 5,324,642 | 6/1994 | Baumgartner . |
| 5,354,654 | 10/1994 | Ligler et al. . |
| 5,466,579 | 11/1995 | Baumgartner ........................ 435/7.1 |
| 5,532,131 | 7/1996 | Lewis . |

FOREIGN PATENT DOCUMENTS

0187862  11/1983  Japan .

OTHER PUBLICATIONS

E Harlow et al. In: Antibodies: A Laboratory Manual, Cold Spring Harbor Laboratory, pp. 683–686, 1988.
RF. Cook et al. Inter. J. Addiction, 30: 403–426, 1995.
H. Sachs et al. Forensic Sci. Inter. 63: 207–216, 1993.
F. Tagliaro et al. J. Chromat. B, 689: 261–271, Feb. 1997.
J. Segura. In: Hair Analysis in Forensic Toxicology, Proceedings of the International Conference and Workshop, Abu Dhabi Police, (Eds) RA de Zeeuw et al. Nov. 19–23, 1995. Forensic Science Labs., General Directorate of Abu Dhabi Police, Abu Dhabi, p. 351, 1995.
K. Aoki et al. J. Pharm. Dyn. 6: 33–38, 1983.
P. Suttijitpaisal et al. Asian Pac. J. Allerg. Immunol. 10: 159–164, 1992.
DL. Colbert. Brit. J. Biomed. Sci. 51: 136–146, 1994.
C. Jurado et al. Forensic Sci. Inter. 70: 165–170, 1995.
T. Mieczkowski. Forensic Sci. Inter. 79: 83–91, 1995.

*Primary Examiner*—James C. Housel
*Assistant Examiner*—S. Devi
*Attorney, Agent, or Firm*—Quirk & Tratos

[57] ABSTRACT

A method for conducting a screening test series for indications of use of drugs of abuse is set forth including enzyme linked immunosorbant assay (ELISA) and radioimmunoassay (RAI) for various analytes extracted from hair samples is set forth. The collected hair sample is divided into portions. One portion is screened cannabinoids using ELISA. Another portion is screened for opiates, PCP, amphetamines and methamphetamines using a combination of RIA or ELISA. Results deemed positive from the screening series are confirmed positive or negative by known techniques such as gas chromatography-mass spectrometry. Those deemed negative are so reportable without the necessity of the expensive confirmatory procedures.

3 Claims, No Drawings

METHOD FOR FORENSICALLY SCREENING HAIR SAMPLES FOR THE PRESENCE OF CANNABINOIDS

FIELD OF THE INVENTION

The present invention relates to forensically acceptable methods for screening samples of hair to determine the presence of indicators of use of drugs of abuse.

BACKGROUND OF THE INVENTION

Testing of hair samples for the presence of indicators of drug use has gained importance not only for evidence gathering for criminal justice system proceedings but in pre-employment and post-employment screening of individuals. Unlike urine or blood sample testing which can provide only short term information concerning drug use by the tested individual and can therefore produce a negative result through abstention preceding the taking of the sample, hair testing can provide a long-term history of drug use for periods of, for example, ninety days or more preceding the taking of the sample. For this reason hair testing for drug use has become a reliable and important pre-employment or periodic test which cannot be defeated by short term abstention.

Heretofore testing of hair samples for drug use of marijuana, phencyclidine (PCP), opiates, cocaine, amphetamine and methamphetamine has been through techniques such as radioimmunoassay (RIA), gas chromatography-mass spectrometry (GC/MS) and tandem gas chromatography-mass spectrometry (GC/MS/MS). These techniques not only qualitatively produce data indicative of the presence or absence of indicators of drug use from a hair sample but also quantify those results. These assays are expensive and time consuming. What is needed is a relatively fast and economical method for conducting a series of screening tests which identify clearly negative samples, i.e. samples with no, or less than threshold amounts, of indicators of use of such drugs, from samples which are positive or not clearly negative. By performing a screening test series on the samples, the necessity of performing complicated, expensive and time consuming assays including GC/MS or GC/MS/MS on determined negative samples would be obviated. Such elaborate assays would be reserved for those samples which, by the screening series, were positive or otherwise not clearly identifiable as negative. Reserving the use of GC/MS and like assays, to samples which are not identified by the screening series as clearly negative, would result in savings in time, reduced workload schedule for expensive assay equipment as well for laboratory personnel.

An appropriate series of screening tests, is a series forensically sustainable in their own right and accordingly must use generally accepted scientific techniques and principles.

Enzyme linked immunosorbant assay (ELISA) has been used for analyzing urine and blood samples to determine the presence of cannabinoids. ELISA is, compared to the other assays such GC/MS and GC/MS/MS, relatively inexpensive, fast and accurate to determine the presence of target analytes indicative of use of certain drugs of abuse. However, attempts to use ELISA as a screening test for cannabinoids on hair sample extracts has heretofore been unsuccessful. ELISA relies upon immunospecific reactions of the analytes to test for the presence of substances. ELISA testing is well known, is described in U.S. Pat. No. 4,952,517 issued Aug. 28, 1990 and accordingly will not be described herein. It is believed that procedures heretofore used for obtaining the hair extract containing the many cannabinoid analytes have been frustrated by adherence of these analytes or unknown amounts thereof on analytical surfaces resulting in the inability to correlate the results of the assay with the actual presence or absence of the analytes being tested for. Accordingly ELISA has not been successful as a test for cannabinoid analytes extracted from hair samples.

It would be useful if ELISA for cannabinoids could be incorporated into a sample screening test series.

It has been known to use ELISA to sample for amphetamine and methamphetamine analytes in urine and blood samples. However, to our knowledge such sampling has not been used on hair samples as part of an overall series of sample screening tests.

It is also known to use radio immunoassay (RIA) to test hair samples for the presence of analytes indicative of use of opiates, cocaine and PCP. RIA, as is known, tags target analytes with a radioactive marker which can be scanned for and read.

SUMMARY OF THE INVENTION

There is set forth, according to the present invention, a method for conducting a screening test series including ELISA and RIA for various analytes extracted from a hair sample and linked to use of drugs of abuse.

Toward this end the method includes dividing a hair sample into measured first and second portions and an aliquot third portion. The first sample portion will be subjected to a screening assay using ELISA to determine whether cannabinoid analytes are present in concentrations exceeding a predetermined threshold amount indicative of use of marijuana. Concentrations below the threshold will be reported as negative and those above the threshold are, subject to confirmation, deemed presumptively positive. The second portion is sampled for opiates, PCP, amphetamines and methamphetamines using a combination of RIA or ELISA screening assays. If the screening tests show concentrations below predetermined thresholds, the sample is deemed negative for use of these drugs of abuse. Those whose concentrations exceed the threshold are deemed presumptively positive and subjected to confirmation. For samples deemed positive by the aforementioned screening tests, a third, aliquot portion, is subjected to a confirmatory assay using GC/MS or GC/MS/MS.

Regarding the screening test for cannabinoids, this step of the method is generally directed to preparation of a chemically stable "cocktail" hair extract which contains cannabinoid analytes in such a manner that the cocktail is susceptible to analysis by ELISA to determine, qualitatively, the concentration of cannabinoid analytes in the extract and whether the cannabinoid concentration is above the predetermined threshold amount.

The method includes preparation of the cocktail for ELISA analysis by introducing the hair sample first portion of a known quantity to a liquid mixture of an inorganic base and aliphatic alcohol and incubating the mixture to extract cannabinoid analytes from the hair into the solution. After incubation, a buffer according to a further aspect of the present invention is added, the buffer including at least one of (a) a phosphate buffer, (b) proteinaceous substance, (c) a non-ionic surfactant and (d) a polyhydric alcohol. Thereafter the method includes evaporating the aliphatic alcohol and polyhydric alcohol, if any alcohol of the mixture preferably in a nitrogen atmosphere. The extract containing the cannabinoid analytes is thereafter analyzed using enzyme linked immunosorbant assay (ELISA) specifically targeting for cannabinoids along with suitable controls.

The buffer for use in the method according to the present invention preferably is substantially 2.653 Gm $KH_2PO_4$, 3.8 Gm $Na_2HPO_4$, 1.0 gm bovine albumin, 100 mg TRITON X ®, a non-ionic surfactant 5 ml or other suitable surfactant and 5 ml ethylene glycol (sterile)dissolved in one liter of deionized water.

DESCRIPTION

The hair sample from the subject to be tested for use of drugs of abuse is collected in the same manner as are hair samples for other types of assays, i.e. RIA, GC/MS and GC/MS/MS. The hair sample is taken from the subject and from the root end of the hair sample, the hair is cut into a length of approximately 3.9 cm. Typically 3.9 cm of growth represents the history for the subject of approximately ninety days. The 3.9 cm length of hair is cut into small pieces of 1 to 2 mm long and the cut pieces are mixed thoroughly. From the mixed pieces, a weighed 20mg portions of the cut hair is transferred into a test tube suitably labeled and hereinafter referred to as "M" to be used for testing for the presence of analytes indicative of use of multiple drugs and to a second tube suitably marked, as for example, "T", to be used for screening analysis for cannabinoid analytes. The remaining, aliquot portion is retained and suitably labeled. The aliquot portion will be used for confirmatory assays if required.

SCREENING ASSAYS FOR MULTIPLE DRUGS

1. Controls.

To provide controls for the screening assays on the sample contained in tube M, controls and calibrators are prepared as hereinafter described. To prepare the hair screening calibrators for testing for multiple drugs, in a 100 ml volumetric flask the following available stock standards are added and then the mixture is diluted with 1:1 methanol in water according to Table I.

TABLE I

| Stock 1 mg/mL Standard | Equivalent in pg/mg of hair |
| --- | --- |
| Methamphetamine | 300 pg/mg |
| Morphine | 300 pg/mg |
| Cocaine | 300 pg/mg |
| Phencyclidine | 300 pg/mg |

Also for the screening test, quality control samples are prepared. A low control is prepared similar to that of the calibrator by adding the following stock standards to a 100 mL volumetric flask and diluting to the mark with 1:1 methanol in water according to Table II.

TABLE II

| Stock 1 mg/mL Standard | Equivalent in pg/mg of hair |
| --- | --- |
| Methamphetamine | 200 pg/mg |
| Morphine | 200 pg/mg |
| Cocaine | 200 pg/mg |
| Phencyclidine | 200 pg/mg |

Similarly a high control is prepared again by diluting the following stock standards to 100 mL in a volumetric flask according to Table III.

TABLE III

| Stock 1 mg/mL Standard | Equivalent in pg/mg of hair |
| --- | --- |
| Methamphetamine | 400 pg/mg |
| Morphine | 400 pg/mg |
| Cocaine | 400 pg/mg |
| Phencyclidine | 400 pg/mg |

With the calibrators and high and low controls prepared, preparation of the sample for testing for multiple drug analytes will now be described.

2. Preparation of First Sample Portion "M".

To each M tube 1 ml of methanol is added, swirled and dumped. 2 mL of methanol is then added and the solution incubated at 70° to 75° C. for two hours. If, after one hour the methanol is evaporated, 500 μL of methanol can be added. With a pipette the solution is transferred to a suitably labeled 12×75 mm test tube. The solution of the test tube is evaporated to remove the methanol under nitrogen at 55° C. and no more than 3.5 psia. After the tube cools, 600 μL of 46 mM phosphate buffer (pH 7.0) is added to each tube and mixed therein. The solution therein defines the hair extract containing the targeted analytes.

To conduct the screening assay for the targeted analytes, 1 mL of negative hair matrix in methanol is added to each of the calibrator and low and high controls, the solution evaporated to dryness. Negative hair matrix consists of 20 mg of hair containing negative concentrations of the targeted analytes which is washed and extracted in the same way as the test sample. The calibrator, high control and low control tubes are then reconstituted by adding 1200 μL of 46 mM phosphate buffer (pH 7.0) as well as adding the buffer to a blank tube. The calibrator, controls, blank and sample can then be placed upon an automated assay machine such as a Mark 5 robotic pipettor manufactured by Diagnostics Products Corporation.

At the same time, the test sample according to the above can be assayed by ELISA for analytes associated with the use of amphetamines and methamphetamines. Using ELISA plates which may be obtained from Diagnostic Ltd, 4730 Coopers Ave. #27, Missisaugua, Ontario, Canada sold as a methamphetamine kit, sufficient ELISA well strips are selected to accommodate all of the samples, calibrators and controls requiring methamphetamine and amphetamine analysis. The automated analysis machine will pipette 2 μL of each sample plus 5 μL of buffer and 100 μL of enzyme conjugate (supplied with kit) into the appropriate well of the ELISA plate.

RIA coated tubes for opiates, cocaine and PCP are obtained from a suitable supplier such as Diagnostic Products Corporation, 5700 West 96th Street, Los Angeles, Calif. and sold as Coat-A-Count®.

The automated device will dispense 25 μL of sample buffer, 1 mL of reagent and the calibrator, controls and sample into the RIA coated tubes. After pipetting of the solutions into the tubes is completed, the racks are covered with parafilm and incubated according to the following times: cocaine, 2 hours, opiates, 1 hour, PCP, 1 hour. After incubation is completed, the tubes are decanted and allowed to drain for 10 to 15 minutes. The tubes are thereafter placed in a gama counter to read their results according to DPC procedure selecting the appropriate drug for reading. The reading includes the sample, low control, high control and whether any of the test samples read positive as compared to the calibrator. Those test samples which read positive compared to the calibrator are deemed to be positive test results.

Those samples which read negative compared to the reading of the calibrator are deemed negative.

Turning it to the ELISA for amphetamine and methamphetamine, the automated analysis machine pipettes 20 mL of each sample plus 5 µL buffer and 100 µL of enzyme conjugate into the well. The machine also pipettes standards and controls into other identified wells. Once pipetting is complete, the pipetting (plates) are incubated for 30 minutes at room temperature, the liquid decanted and the ELISA plate is washed once to stop the reaction and the water is decanted. Each well is washed six times with a wash buffer. Thereafter 100 µL of substrate reagent is added to each well and incubated for 20 to 30 minutes in the dark at room temperature. After incubation 100 µL of stopping reagent is added to each well and the absorbance using a plate reader set at 450 nm for peak and 630 nm for background absorbance is used. A darker color of the ELISA well indicates a lower concentration of analytes associated with use of amphetamines and methamphetamines. By optically reading the ELISA plates, negative samples can be qualitatively determined based upon color as determined by light absorbance. Those samples not deemed negative are believed to contain the concentrations exceeding the threshold established by the high and low screening controls.

The samples deemed negative for use of the targeted drugs are reported as such. Those deemed positive are scheduled for quantitative confirmatory analysis according to GC/MS or GC/MS/MS.

3. Screening Analysis For Cannabinoid Analytes.

As disclosed in our co-pending application entitled Method for forensically screening hair samples for the presence of cannabinoids, the hair for testing for multiple drugs and for testing according to the present invention may be incorporated into an overall system for preliminary screening of target analytes through a diversified series of immunoassays including ELISA and RIA to determine the presence or absence of target compounds in the hair samples. If positive preliminary results are obtained, GC/MS or GC/MS/MS assays may be used to measure, confirm and certify the amount of the target analyte present in the sample.

While as stated above, the hair sample in the test tube marked "M" for multiple drug assay can be used for the diversified series of immuno-assays described above, the present invention is directed to the second sample of hair which is marked "T" and is dedicated to the screening assay for cannabinoid analytes.

To the tube containing the hair sample to be tested for cannabinoids, 1 mL of 1% wash solution is added to wash the exterior of the hair to remove any environmentally implicated compounds. The solution is preferably a mix of 10 mL of Nexus® clarifying treatment shampoo with 1 L of deionized water. After the hair sample and wash solution is left standing for 10 minutes at room temperature, the tube is swirled and the liquid is decanted. 2 mL of deionized water are added, the tube is swirled and the liquid decanted immediately. The washing with the deionized water is repeated again.

After washing of the hair sample, 1 mL of acetone is added to the tube, left standing 5 minutes for room temperature, the tube swirled and dumped. The foregoing washing steps prepare the hair sample for extraction of cannabinoid analytes according to the method of the present invention.

The cannabinoid analytes of the hair sample are extracted by adding an extraction solution consisting of a mixture of an inorganic base and an aliphatic alcohol, preferably 0.1% (v/v) ammonium hydroxide in methanol. For a 20 mg hair sample it has been found that 2 mL of the extraction solution is sufficient. After the extraction solution has been added, the mixture is incubated to promote extraction of the cannabinoid analytes from the hair sample. Preferably according to the method of the present invention, incubation consists of heating the test tube at 70° to 75° C. for 2 hours.

Subsequent to incubation, the test tube is cooled and the liquid extract of the tube is transferred to one or more 12×75 mm test tubes. The original test tubes and hair are discarded. To each of these test tubes a blocking buffer solution according to the present invention is added. The buffer solution includes at least one of a phosphate buffer, a proteinaceous substance, a non-ionic surfactant and a polyhydric alcohol. Preferably the blocking buffer solution is prepared by adding to a 1L flask the following: 2.653 Gm of $KH_2PO_4$, 3.80 Gm $Na_2HPO_4$, 1.0 Gm bovine albumin, 100 mg TRITON X®, a non-ionic surfactant and 5 ml ethylene glycol (sterile) dissolved in one liter of deionized water. The solution is diluted to 1 L with distilled water and mixed. The solution should be checked to determine that the pH is 7.0±0.5. The prepared buffer solution can be stored under refrigeration for limited periods of time at between 2° to 8° C. Approximately 25 µL of the blocking buffer is added to each of the 12×25 mm test tubes containing the hair extracts.

Thereafter, the methanol of the hair extract solution and buffer solution is evaporated preferably under a stream of dry nitrogen at 55° C. The nitrogen preferably is set at a pressure no greater than 3.5 psia.

Controls and Calibrators

To control and calibrate for ELISA, a calibrator tube is provided and into which is added 150 µL of ELISA THC calibrator containing 6 ng per mL of delta-9-THC. This calibrator will serve to provide a known concentration of cannabinoid analytes (THC) for calibrating ELISA. To the tube containing the ELISA THC screen calibrator is added approximately 25 µL of the buffer solution described above. The methanol is thereafter evaporated under dry nitrogen at 55° C. and at a pressure of no more than 3.5 psia. To the calibrater tube, after evaporation is added 2.160 µL of 46 mM phosphate buffer (pH 7). After the addition of the phosphate buffer, the calibration solution is prepared.

To serve as controls, there are also provided ELISA THC screen low and high controls. The low control contains user hair previously assayed to contain 3 to 10 picograms of THC per mg. The high control contains user hair previously assayed to contain 40 to 100 picograms of THC per mg. These low control and high control samples are extracted according to the method described above in reference to the test samples.

The ELISA Test

The ELISA assay of the test sample, control samples and calibrator is in accordance with the instructions provided with ELISA plates kits for THC which can be obtained from Diagnostic Ltd referred to above which are used for urine and/or blood samples. A robotic pipettor can be preprogrammed to run the analyses of numerous test samples as well as controls as is well known in the art.

The test sample, control samples and calibrator are pipetted into the ELISA wells along with a kit provided enzyme conjugate. The samples are incubated for approximately 60 minutes at room temperature. During the incubation period the enzyme conjugate competes with the analytes in the sample for binding sites on an analyte targeting antibody coated in the ELISA well.

After incubation, the samples are decanted from the wells and the wells are washed as by submerging the ELISA plate in a water bath. The washing water is removed from the wells.

Thereafter approximately 100 μL of enzyme conjugate supplied with the kit is added to each well and the plate is incubated for 30 minutes. After the aforesaid incubation period, the conjugate is decanted, the plates are washed with water and the wells are thereafter washed approximately 6 times with a wash buffer typically supplied with the ELISA plate kit. 100 μL of a substrate reagent, also supplied with the ELISA kit, is added to each well and the plates are incubated for 20 to 30 minutes in the dark at room temperature until the color in the wells appears developed. The development of the color by addition of the substrate reagent is inversely proportional to the concentration of the targeted analyte. That is, a darker color indicates a lower concentration.

After the incubation period 100 mL of kit supplied stopping reagent is added to each well. A plate reader which optically reads the color concentration of the well is used to read the test results and is typically set at wavelengths of 450 nm and 630 nm. Scanning the calibrator and control samples serves as a control for the reading of the analyses since these controls have known amounts of the targeted analyte.

It has been found that by using the method and the buffer solution described above, the screening test using ELISA can qualitatively determine the presence of cannabinoid compounds in a hair sample in concentration ranges from femtograms to picograms per milligram of sample. Furthermore the screening analyses using ELISA is economical when compared to other assays such as GC/MS or GC/MS/MS due to savings and time, manpower and equipment. By using the ELISA screening test, clearly negative samples need not be subjected to the complicated assays thereby saving this expensive procedure for confirmatory assays of positive or marginal tests.

While we have described certain embodiments of the method for forensically analyzing hair samples for the presence of cannabinoids and a buffer for use therein, it is to be understood that the invention is subject to modifications without departing from the spirit and scope of the claims herein.

We claim:

1. A method for determination of use of drugs of abuse from a hair sample comprising:

(i) dividing the hair sample into substantially equal first and second portions and an aliquot third portion;

(ii) determining the concentration of cannabinoid analytes using an enzyme linked immunosorbent assay (ELISA) test kit for cannabinoids by adding a mixture of an inorganic base and an aliphatic alcohol, said inorganic base being in a concentration of approximately 0.1%, to the sample first portion, incubating the mixture and portion thereby releasing said analytes into the mixture solution, introducing to the incubated mixture solution a buffer solution including (a) a phosphate buffer, (b) a serum protein, (c) a non-ionic surfactant and (d) a polyhydric alcohol, evaporating the alcohol of the mixture and buffer solution in a nitrogen atmosphere and analyzing the evaporated mixture using the ELISA test kit;

(iii) running a screening series on the second portion for other analytes linked to use of drugs of abuse including, (a) performing ELISA assay to determine the concentrations of amphetamine and methamphetamine analytes, and (b) performing a radio immunoassay for cocaine, opiates and phencyclidine derived analytes to determine the concentrations of analytes linked to use of said compounds;

(iv) comparing the concentrations of analytes determined from (ii) and (iii) to preselected threshold analyte concentrations, determined concentrations below said thresholds deemed a negative finding and concentrations above said thresholds deemed a presumptively positive finding; and (v) for samples having a presumptively positive finding, subjecting the sample third portion to confirmatory assay by gas chromatography/mass spectrometry to quantitatively determine the concentrations of said analytes.

2. The method of claim 1 wherein the introducing step includes introducing a buffer solution where the phosphate buffer is selected from the group consistinq of potassium phosphate and sodium phosphate and the polyhydric alcohol is ethylene glycol.

3. The method of claim 2 wherein the introducing step includes introducing a buffer substantially consisting of 2.653 gm $KH_2PO_4$, 3.8 gm $Na_2HPO_4$, 1.0 gm bovine albumin, 100 mg non-ionic surfactant and 5 mL ethylene glycol.

* * * * *